(12) United States Patent
Suga

(10) Patent No.: US 6,355,011 B2
(45) Date of Patent: *Mar. 12, 2002

(54) APPLICATOR WITH SANITARY TAMPON

(75) Inventor: Ayami Suga, Kagawa-ken (JP)

(73) Assignee: Uni-Charm Corporation, Ehime-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/536,408

(22) Filed: Mar. 28, 2000

(30) Foreign Application Priority Data

Mar. 31, 1999 (JP) .......................... 11-092665

(51) Int. Cl.⁷ ............................... A61F 13/20
(52) U.S. Cl. ...................................... 604/15
(58) Field of Search ...................... 604/11–18, 285–288

(56) References Cited

U.S. PATENT DOCUMENTS 3,762,413 A * 10/1973 Hanke .......................... 604/14
3,765,417 A    10/1973 Crockford
4,077,408 A     3/1978 Murray et al.
4,620,534 A    11/1986 Zartman
5,643,196 A *  7/1997 Child et al. ................... 604/14
5,674,239 A    10/1997 Zadini et al.

FOREIGN PATENT DOCUMENTS

EP   0 104 039    3/1984
FR   2 546 399   11/1984
GB     561 173    5/1944
WO   82 02489    8/1982

* cited by examiner

Primary Examiner—Dennis Ruhl
(74) Attorney, Agent, or Firm—Lowe Hauptman Gilman & Berner, LLP

(57) ABSTRACT

An applicator with a sanitary tampon includes an outer cylindrical tube and an inner plunger axially movable within the outer cylindrical tube for ejecting the tampon out of a front end opening of the outer cylindrical tube. The outer cylindrical tube is dimensioned to be longer than a length of the tampon by 50~80 mm.

5 Claims, 2 Drawing Sheets

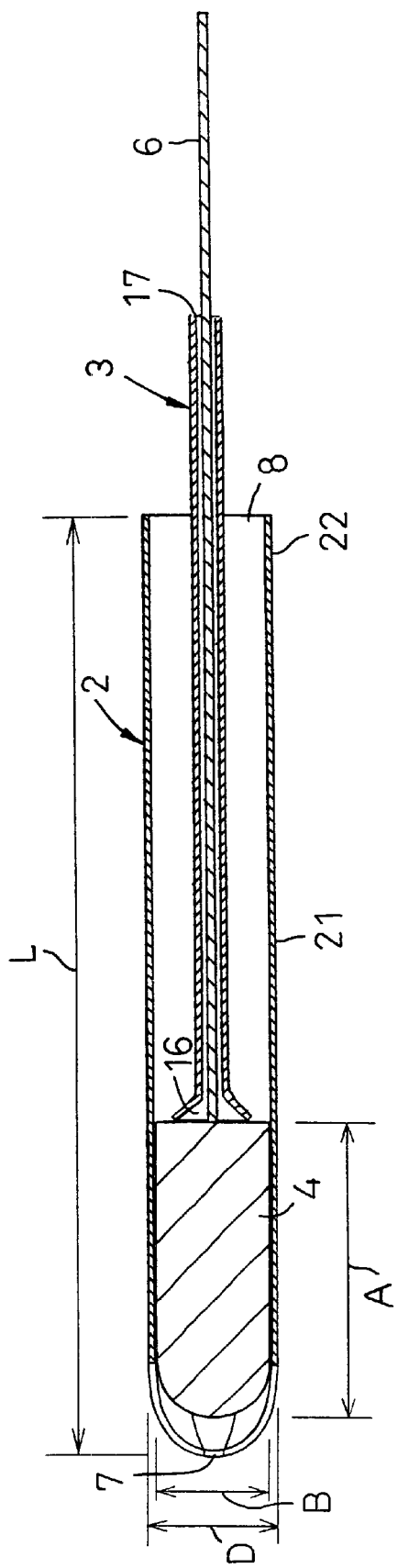

APPLICATOR WITH SANITARY TAMPON

BACKGROUND OF THE INVENTION

This invention relates to an applicator with a sanitary tampon and more particularly to such an applicator used to insert this tampon into a vaginal a canal of the user.

Japanese Patent Application Disclosure No. 1980-155647 describes an applicator for a sanitary tampon comprising an outer cylindrical tube and an inner plunger axially movable within the outer cylindrical tube for ejecting a sanitary tampon out of its front end opening into the vaginal canal. The outer cylindrical tube has a length substantially corresponding to a length of the tampon cased by the applicator plus a length appropriate to hold the applicator with the user's finger tips (i.e., a length of a grip region).

This applicator is used in a manner such that, after the outer cylindrical tube has been inserted into the vaginal canal, the tampon cased within the outer cylindrical tube is axially pushed by the inner plunger into the innermost region of the vaginal canal. The outer cylindrical tube generally has a full length of 70~80 mm of which a partial length of 10~20 mm is defined by the grip region, i.e., a region of the outer cylindrical tube to be actually inserted into the vaginal canal has a length of 50~70 mm. A length of the tampon cased within this region is in a range of 45~55 mm. It should be noted here that there is a sphincteral muscle around the vaginal opening and the tampon may continue to press the sphincteral muscle and give the user a sense of incompatibility unless the tampon was pushed forward into the innermost region of the vaginal canal. To avoid such a sense of incompatibility, it is desired that the tampon should be pushed forward far from the sphincteral muscle, more specifically, into the innermost region of the vaginal canal spaced from the vaginal opening by 40~50 mm or more. With the known applicator, its length to be actually inserted into the vaginal canal corresponds to the full length of the outer cylindrical tube minus the length of the grip region, i.e., 70~80 mm–10~20 mm=50~70 mm. Accordingly, it is concerned that the tampon might be stayed in a region spaced from the vaginal opening at most by 40~50 mm and give the user a sense of incompatibility unless most of the length of the insertion region is pushed into the vaginal canal. Even if once the outer cylindrical tube has been pushed into the innermost region of the vaginal canal, a vaginal pressure functions to obstruct the tampon be held in the innermost region and to push the tampon back. As a result, the tampon might be at least partially stayed in a region spaced from the vaginal opening by 40~50 mm and give the user a sense of incompatibility. Thus, use of the tampon might result in failure.

SUMMARY OF THE INVENTION

It is an object of this invention to provide a sanitary tampon combined with an applicator improved to avoid a failure in use of the tampon often encountered by the prior art.

According to this invention, there is provided an applicator with a sanitary tampon, the applicator comprising an outer cylindrical tube having openings at front and rear ends thereof and an inner plunger axially movable within the outer cylindrical tube and the tampon cased within a region of the outer cylindrical tube adjacent the front end thereof and adapted to be ejected by the inner plunger out of the opening of the front end, wherein the outer cylindrical tube has a length dimensioned to be longer than a length of the tampon by 50~80 mm.

According to one preferred embodiment of this invention, said tampon has a length of 20~60 mm.

BRIEF DESCRIPTION OF THE DRAWINGS

FIG. 2 is a sectional view taken along line II—II in FIG. 1.

DETAILED DESCRIPTION OF THE PREFERRED EMBODIMENTS

Figure 1:
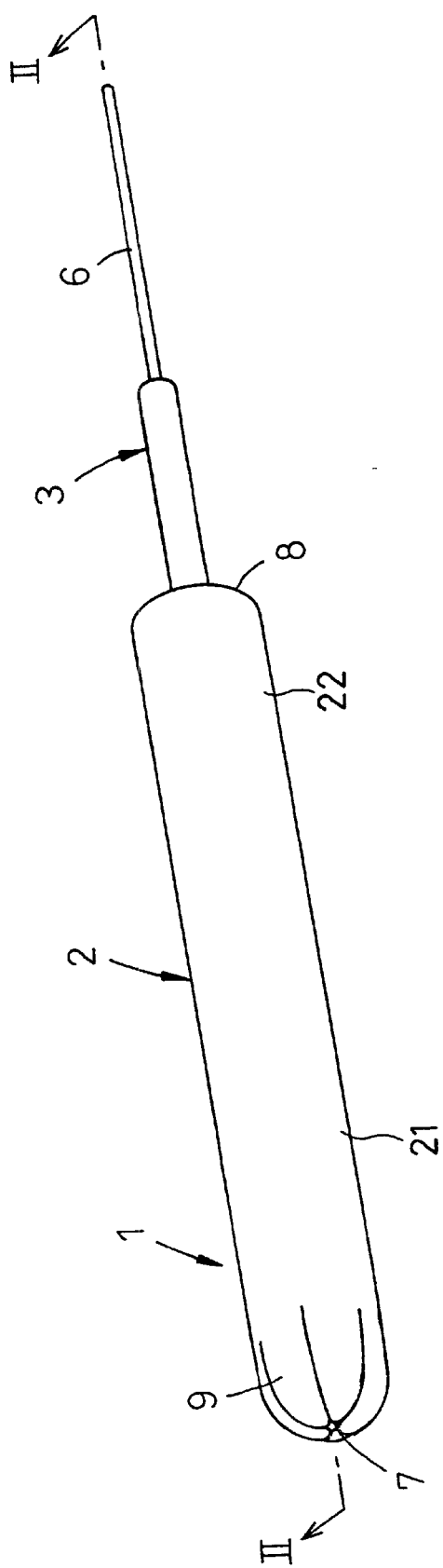
FIG. 1 is a perspective view depicting a sanitary tampon combined with an applicator as one embodiment of this invention.

An application with a sanitary tampon according to this invention will be described in more detail with reference to the accompanying drawings.

FIG. 1 is a perspective view depicting an applicator with a sanitary tampon and FIG. 2 is a sectional view taken along line II—II in FIG. 1. An applicator 1 comprises an outer cylindrical tube 2 casing therein, a tampon 4, and an inner plunger or piston 3 axially movable within the outer cylindrical tube 2. The inner plunger 3 is also in the form of tube. The tampon 4 is provided on its rear end with a string 6 extending rearward through the inner plunger 3 beyond a rear end of the inner plunger 3.

The outer cylindrical tube 2 has openings 7, 8 at its front and rear ends. The front end opening 7 is normally covered with a plurality of elastically deformable petal-like portions 9 and the inner plunger 3 extends rearward through the outer cylindrical tube 2 beyond its rear end opening 8. A full length L of the outer cylindrical tube 2 is defined by an insertion region 21 intended to be inserted into the vaginal canal of the user when the tampon 4 is actually used and a grip region 22 intended to be held by the user's fingers. The insertion region 21 has a length corresponding to a full length A of the tampon 4 plus 40~60 mm and the grip region 22 has a length of 10~20 mm. Depending on the full length A of the tampon 4, the full length L may be selected within a range of approximately 70 mm~ approximately 140 mm. While an outer diameter D of the outer cylindrical tube 2 may be appropriately dimensioned so far as the outer cylindrical tube 2 can be smoothly inserted into the vaginal canal, the outer diameter D is preferably dimensioned in a range of 8~20 mm. A wall thickness of the outer cylindrical tube 2 is substantially uniform except the petal-like portions 9.

The outer cylindrical tube 2 configured as has been described above is made of soft and elastic thermoplastic material so that the petal-like portions 9 may be elastically deformed with the minimum resistance to fully open the front end opening 7 and more preferably the outer cylindrical tube 2 as a whole may have a sufficient flexibility to follow a curvature of the vaginal canal.

The inner plunger 3 is a straight element having openings 16, 17 at its front and rear ends, respectively. The front end opening 16 intended to be placed against the rear end of the tampon 4 has its peripheral edge flared like a trumpet so that the string 6 of the tampon 4 may be easily inserted thereinto and the rear end of the tampon 4 may be pushed forward over an area as large as possible. The rear end opening 17 and a region in the vicinity of the opening 17 of the inner plunger 3 extend rearward beyond the rear end opening 8 of the outer cylindrical tube 2. While the inner plunger 3 also has a flexibility, the flexibility of the inner plunger 3 is preferably lower than the flexibility of the outer cylindrical tube 2 in order to ensure that the tampon 4 can be smoothly ejected.

The tampon 4 is cased within a region of the outer cylindrical tube 2 adjacent its front end and provided with the string 6 extending rearward from the rear end of the tampon 4 through the inner plunger 3 beyond its rear end opening 17. The string 6 is used to draw the tampon 4 out from the vaginal canal. The tampon 4 functions to push open the petal-like portions 9 as the tampon 4 is pushed by the inner plunger 3 from behind until the tampon 4 completely leaves the outer cylindrical tube 2. Such tampon 4 has a full length A preferably in a range of 20~60 mm and an outer diameter B dimensioned so that its outer peripheral surface defined by the outer diameter B may be brought in close contact with an inner peripheral surface of the outer cylindrical tube 2.

In actual use of the tampon combined with the applicator, the insertion region 21 is received by the vaginal canal. The tampon 4 lies in front of said insertion region 21 and therefore the rear end of the tampon 4 is spaced from the vaginal opening by dimensional differences between the insertion region 21 and the tampon 4, i.e., 40~60 mm. Such tampon 4 can be stayed within the vaginal canal by pushing the inner plunger 3 into the vaginal canal with the outer cylindrical tube 2 being held or by drawing the outer cylindrical tube 2 out from the vaginal canal with the inner plunger 3 being held. The tampon 4 is held within the vaginal canal's innermost region spaced from the vaginal opening as far as 40 mm or more. Accordingly, it is not concerned that the tampon 4 might exert a pressure upon the sphincteral muscle and give the user a sense of incompatibility due to use of the tampon 4. In the case of the tampon adapted to be used in such a manner in which the outer cylindrical tube 2 is drawn out from the vaginal canal with the inner plunger 3 being held, it is unnecessary to push a firmly compression molded tampon from behind into the innermost region of the vaginal canal as in the prior art. In this manner, this invention allows a relatively soft tampon 4 to be used and such soft tampon 4 advantageously enables menstrual discharge to be rapidly absorbed.

The sanitary tampon combined with the applicator provided by this invention enables the tampon to be reliably positioned within the innermost region of the vaginal canal without giving the user a sense of incompatibility since the applicator is longer than the tampon by 40 mm or more.

What is claimed is:

1. An applicator with a sanitary tampon, said applicator comprising an outer cylindrical tube having an opening at front and rear ends thereof, respectively, and an inner plunger axially movable within said outer cylindrical tube, said tampon being cased within a region of said outer cylindrical tube adjacent said front end thereof and adapted to be ejected by said inner plunger out of said opening of said front end, wherein said outer cylindrical tube has a length dimensioned to be longer than a length of said tampon by 50–80 mm, and said tampon has a length of about 20–49 mm.

2. The applicator according to claim 1, wherein said inner plunger is in the form of tube, and a string provided on a rear end of said tampon extends rearward through said inner plunger beyond a rear end of said inner plunger.

3. An applicator with a sanitary tampon, said applicator comprising an outer cylindrical tube having respective openings at front and rear ends thereof, wherein said front opening is covered with a plurality of elastically deformable petal-like portions which integrally extend from said outer cylindrical tube and an inner plunger which is in the form of a tube and axially movable within said outer cylindrical tube, said tampon cased within a region of said outer cylindrical tube adjacent said front end thereof and adapted to be ejected by said inner plunger out of said opening of said front end, wherein said tampon has a length of about 20–49 mm and said tampon is provided on a rear end thereof with a string extending rearward through said inner plunger beyond a rear end of said inner plunger, wherein said outer cylindrical tube has a length dimensioned to be longer than a length of said tampon by 50–80 mm.

4. An applicator with a sanitary tampon, said applicator comprising an outer cylindrical tube having an opening at front and rear ends thereof, respectively, and an inner plunger axially movable within said outer cylindrical tube, said tampon being cased within a region of said outer cylindrical tube adjacent said front end thereof and adapted to be ejected by said inner plunger out of said opening of said front end, wherein said outer cylindrical tube has a length dimensioned to be longer than a length of said tampon by 50–80 mm, and the flexibility of the inner plunger is less than the flexibility of the outer cylindrical tube to enable the tampon to be smoothly ejected through the front end of the outer cylindrical tube.

5. An applicator with a sanitary tampon, said applicator comprising an outer cylindrical tube having respective openings at front and rear ends thereof, said tampon being cased within a region of said outer cylindrical tube adjacent said front end thereof, said outer cylindrical tube having a substantially constant diameter extending from a portion immediately adjacent the front opening up to the rear opening, and an inner plunger in the form of a tube and being axially movable within said outer cylindrical tube, a front end of said inner plunger engaging a rear end of said tampon, wherein said tampon is provided with a string extending from said rear end rearwardly through said inner plunger and beyond a rear end of said inner plunger, said outer cylindrical tube has a length dimensioned to be longer than a length of said tampon by about 50–80 mm, an inner diameter of said inner plunger is slightly greater than a diameter of said string, and said front end of the inner plunger is outwardly flared toward the rear end of the tampon it is in contact with.

* * * * *